(12) United States Patent
Hong et al.

(10) Patent No.: US 10,000,470 B1
(45) Date of Patent: Jun. 19, 2018

(54) METHOD FOR PREPARING NILOTINIB

(71) Applicants: ASYMCHEM LABORATORIES (TIANJIN) CO., LTD, TEDA Tianjin (CN); ASYMCHEM LIFE SCIENCE (TIANJIN) CO., LTD, TEDA Tianjin (CN); TIANJIN ASYMCHEM PHARMACEUTICAL CO., LTD, TEDA Tianjin (CN); ASYMCHEM LABORATORIES (FUXIN) CO., LTD, Liaoning (CN); JILIN ASYMCHEM LABORATORIES CO., LTD, Jilin (CN)

(72) Inventors: Hao Hong, TEDA Tianjin (CN); Gage James, TEDA Tianjin (CN); Jiuyuan Li, TEDA Tianjin (CN); Changfeng Li, TEDA Tianjin (CN); Gaochao Huang, TEDA Tianjin (CN)

(73) Assignees: ASYMCHEM LABORATORIES (TIANJIN) CO., LTD, Teda Tianjin (CN); TIANJIN ASYMCHEM PHARMACEUTICAL CO., LTD, Tianjin (CN); JILIN ASYMCHEM LABORATORIES CO., LTD, Jilin (CN); ASYMCHEM LIFE SCIENCE (TIANJIN) CO., LTD, Teda Tianjin (CN); ASYMCHEM LABORATORIES (FUXIN) CO., LTD, Liaoning (CN)

( * ) Notice: Subject to any disclaimer, the term of this patent is extended or adjusted under 35 U.S.C. 154(b) by 0 days. days.

(21) Appl. No.: 15/574,528

(22) PCT Filed: May 26, 2015

(86) PCT No.: PCT/CN2015/079854
§ 371 (c)(1),
(2) Date: Nov. 16, 2017

(87) PCT Pub. No.: WO2016/187824
PCT Pub. Date: Dec. 1, 2016

(51) Int. Cl.
*C07D 401/14* (2006.01)

(52) U.S. Cl.
CPC ................. *C07D 401/14* (2013.01)

(58) Field of Classification Search
CPC .................................... C07D 401/14
See application file for complete search history.

(56) References Cited

U.S. PATENT DOCUMENTS

2010/0016590 A1* 1/2010 Wang .................. C07D 233/61
544/297

* cited by examiner

*Primary Examiner* — Bruck Kifle
(74) *Attorney, Agent, or Firm* — Porter Wright Morris & Arthur, LLP

(57) ABSTRACT

A method for preparing nilotinib includes the following steps: performing an aminocarbonylation reaction on a compound A and 3-(4-methyl-1H-imidazole-1-yl)-5-(trifluoromethyl) aniline to obtain an amination product; and performing deprotection treatment of an R group on the amination product to obtain the nilotinib, wherein the compound A has a structure shown in formula I, and in formula I, an R group is selected from benzyl, —COCF$_3$, —CHO or —CO$_2$R', where an R' group is C$_1$~C$_{10}$ alkyl, C$_1$~C$_3$ alkoxy ethyl or C$_7$~C$_{19}$ aralkyl.

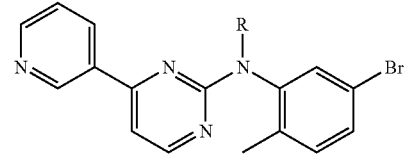

Formula I

20 Claims, 1 Drawing Sheet

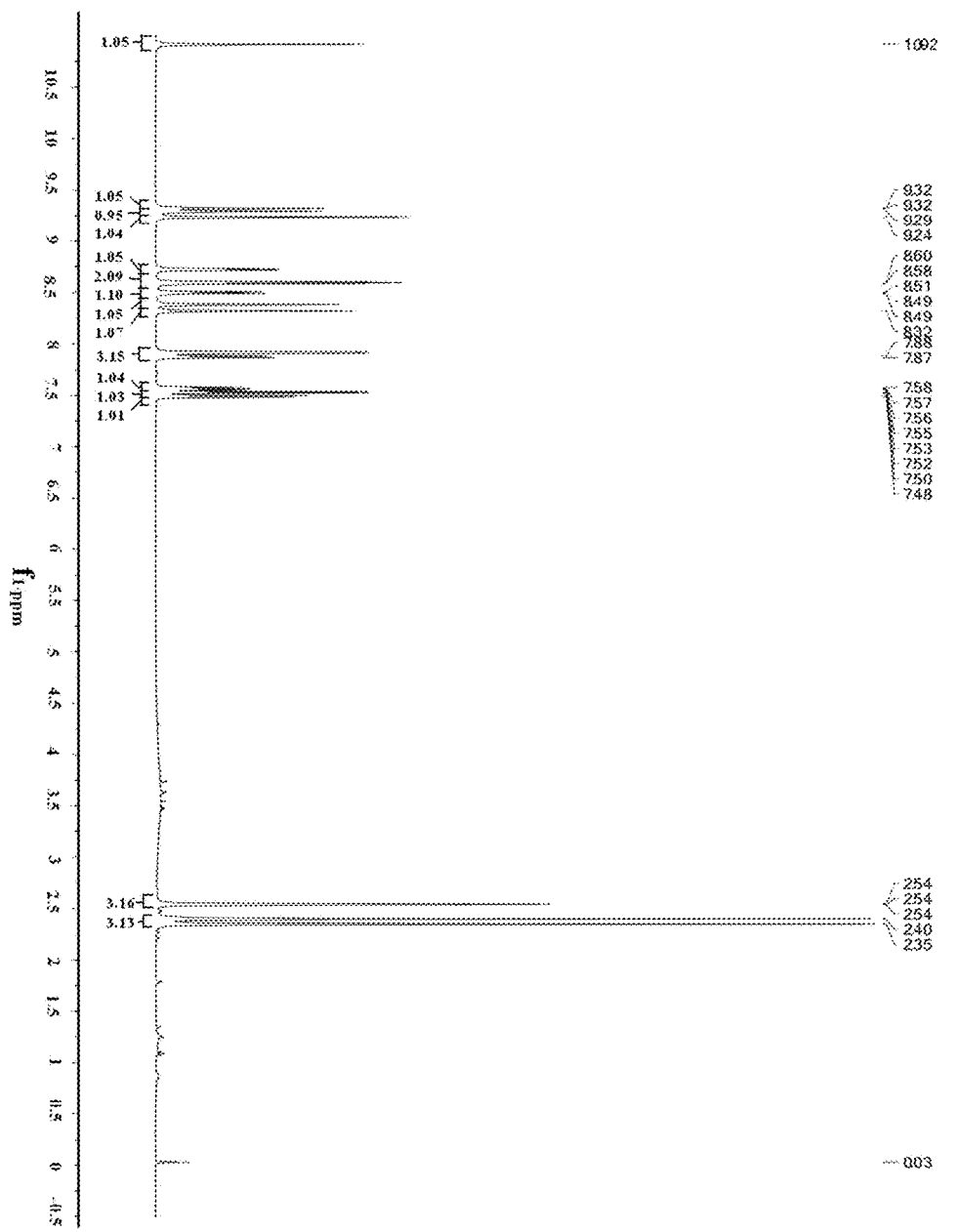

METHOD FOR PREPARING NILOTINIB

TECHNICAL FIELD

The disclosure relates to the field of medicinal chemistry, and particularly to a method for preparing nilotinib.

BACKGROUND

Nilotinib is a potent and accurate second-generation tyrosine-kinase inhibitor, its application range includes an adult patient with a chronic myelogenous leukemia-chronic phase or accelerated phase treatment (including imatinib) history, and a drug-tolerant or intolerant Philadelphia chromosome of the patient is positive.

In existing researches, different synthesis methods for nilotinib are recorded in many patents and documents.

Route 1: in most of existing patents and documents, 3-(4-methyl-1H-imidazole-1-yl)-5-(trifluoromethyl) aniline is adopted as a raw material, and is coupled with 4-methyl-3-(4-(pyridine-3-yl) pyrimidine-2-ylamino)benzoic acid or a derivative thereof to obtain nilotinib.

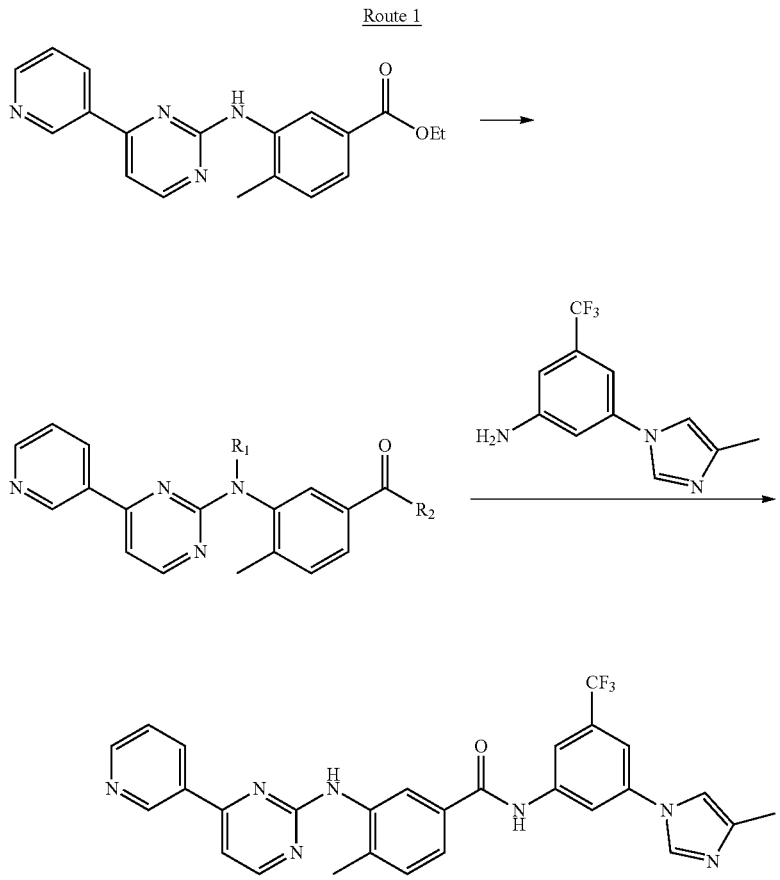

$R_1$ is H, and $R_2$ is OH, Cl, alkoxy or aralkyl; or $R_1$ is OH, and $R_2$ is t-butyloxycarboryl.

Route 2: an arylcarboxylic acid is reacted with 3-bromo-5-(trifluoromethyl)aniline to produce amide, and the amide is further coupled with imidazole to obtain a target molecule nilotinib by a metal catalyst, wherein M is halogen or OH.

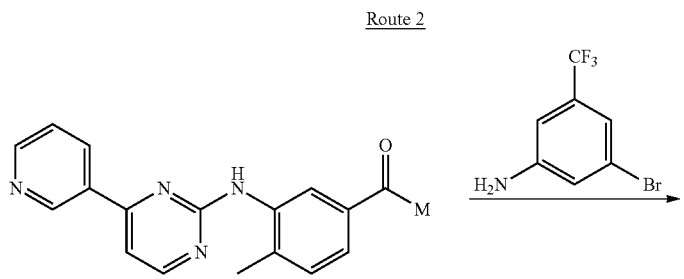

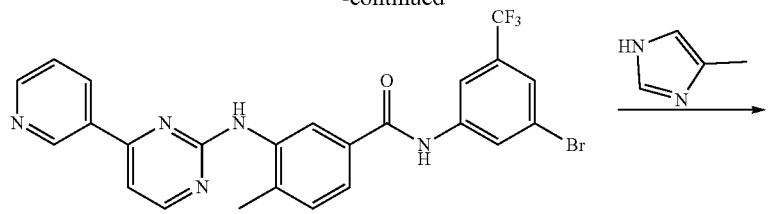
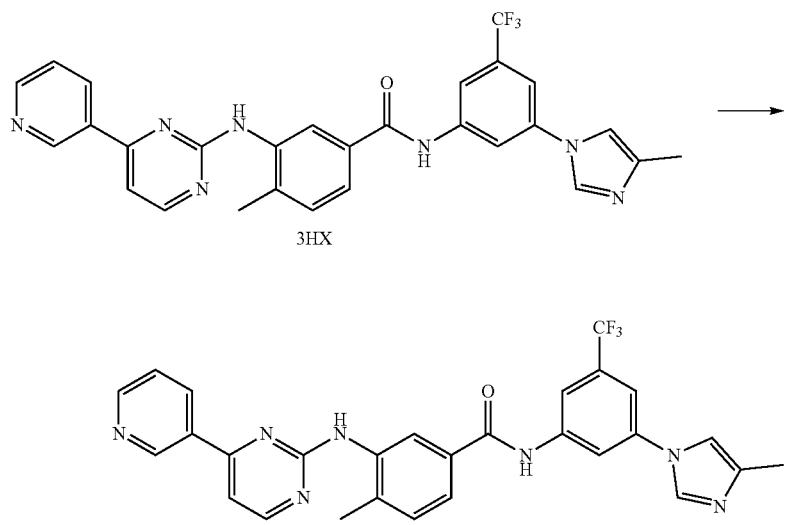
Route 3: 3-(pyridine-3-yl) pyrimidine-1-ylamine and substituted iodobenzene are coupled in the presence of a metal catalyst to obtain a target molecule nilotinib.
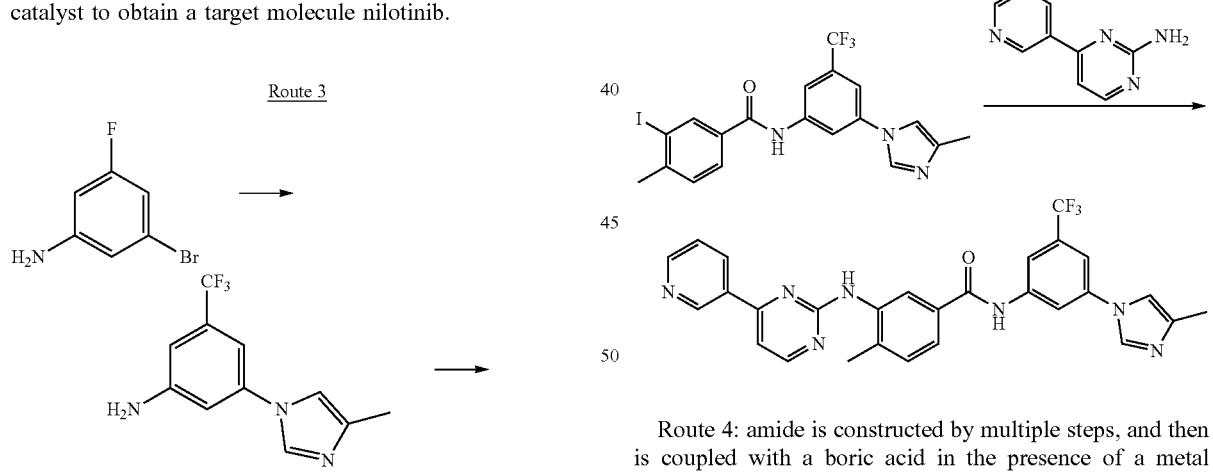
Route 4: amide is constructed by multiple steps, and then is coupled with a boric acid in the presence of a metal catalyst to obtain a target molecule nilotinib.
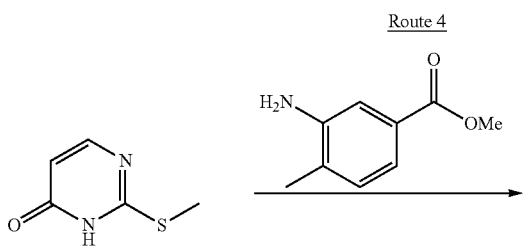

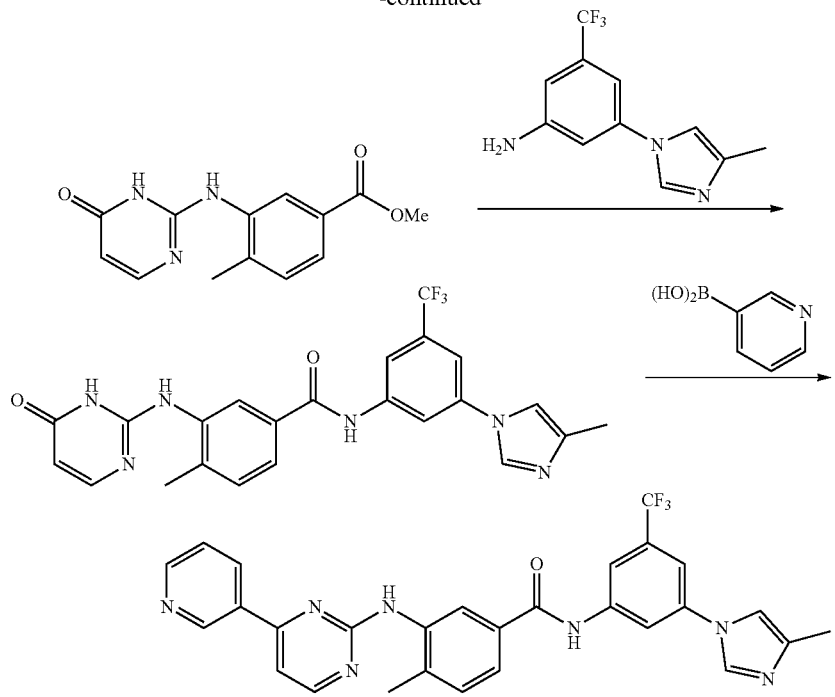
Route 5: 3-nitro-4-methylbenzoyl chloride is reacted with 3-(4-methyl-1H-imidazole-1-yl)-5-(trifluoromethyl)aniline, and substituted aryl guanidine is obtained by multi-step conversion, and then is coupled and condensed with an unsaturated ketone to obtain a target molecule nilotinib.
Route 5
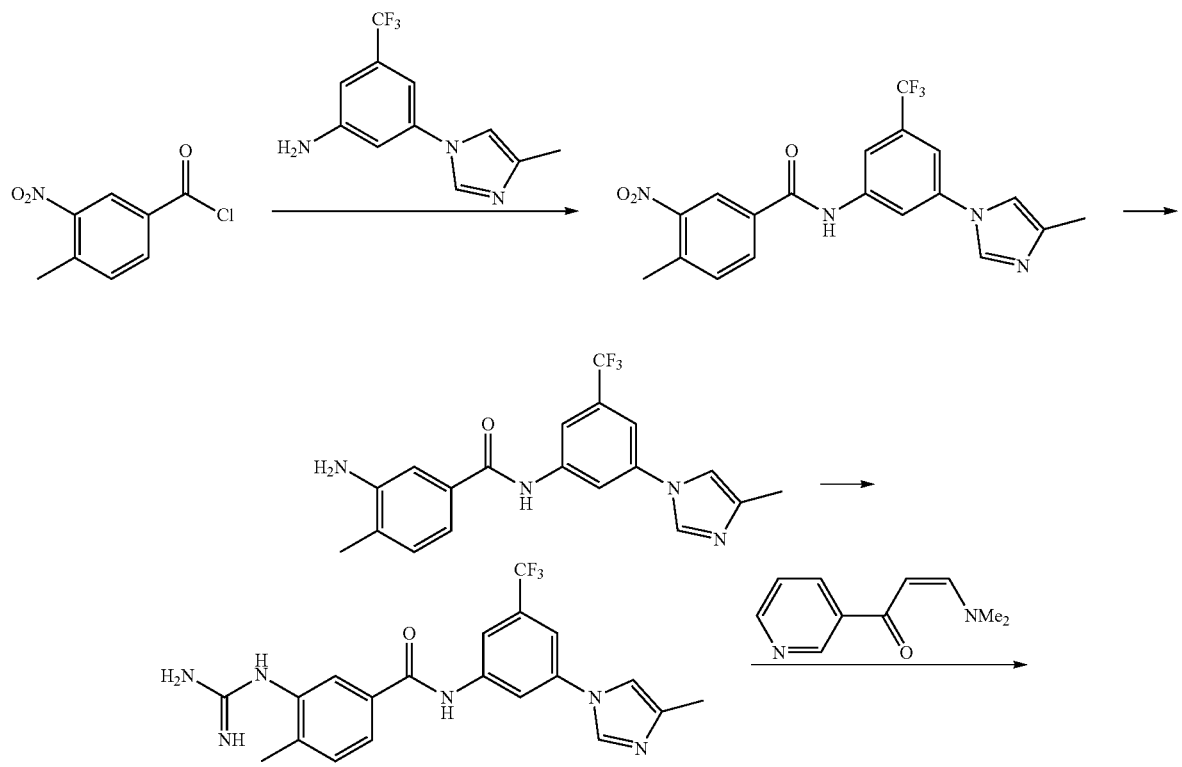

-continued

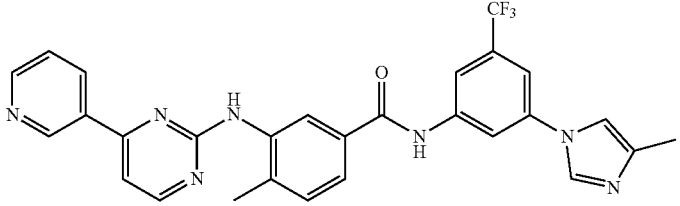

However, the above reaction routes also have some shortcomings: route 1 is excessively high in starting raw material cost, and each of routes 2 to 5 has lengthy synthetic sequences. Because an aromatic amine has poor nucleophilicity (compared with alkyl amines), a high temperature of over 120° C. is usually required when it is used for a palladium-catalyzed aminocarbonylation reaction, and consequently, it is necessary to increase carbon monoxide pressure, which increases a potential safety hazards. In addition, an application of a palladium-catalyzed carbonylation esterification/amination reaction to synthesis of pharmaceutical molecule containing numerous heteroatoms is limited. Since complexion of a nitrogen atom and a metal ion reduces a catalytic activity, a larger using amount of catalyst or a specially structured ligand is usually required to achieve a high yield in such a reaction, and these measures increase cost.

Based on the above problems, it is necessary to develop a novel route for synthesizing nilotinib, which is lower in cost and short in synthesis route.

SUMMARY

The disclosure is mainly intended to provide a method for preparing nilotinib, so as to solve the problems of high route cost and long steps of existing synthesis of the nilotinib.

In order to achieve the purpose, according to an aspect of the disclosure, a method for preparing nilotinib is provided, which includes the following steps: performing an aminocarbonylation reaction on a compound A and 3-(4-methyl-1H-imidazole-1-yl)-5-(trifluoromethyl)aniline to obtain an amination product; and performing deprotection treatment of an R group on the amination product to obtain the nilotinib, wherein the compound A has a structure shown in formula I:

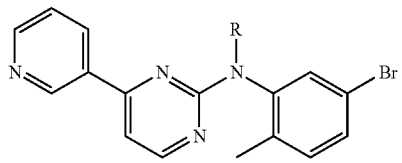

Formula I the R group is selected from benzyl, —COCF$_3$, —CHO or —CO$_2$R', wherein an R' group is C$_1$~C$_{10}$ alkyl, C$_1$~C$_3$ alkoxy ethyl or C$_7$~C$_{19}$ aralkyl.

Furthermore, the aminocarbonylation reaction is performed on the compound A under a condition which include an organic solvent, a catalyst and a carbon monoxide, wherein a molar ratio of the 3-(4-methyl-1H-imidazole-1-yl)-5-(trifluoromethyl)aniline to the compound A is 0.5:1~2:1, and the catalyst is 0.1~20% of a mole number of the compound A.

Furthermore, the catalyst includes a first catalyst and a second catalyst, wherein the first catalyst is selected from one or more in a group formed by PdCl$_2$(PPh$_3$)$_2$, PdCl$_2$(PhCN)$_2$, PdCl$_2$(CH$_3$CN)$_2$, Pd(PPh$_3$)$_4$, Pd$_2$(dba)$_3$CH$_2$Cl$_2$, PdCl$_2$(dppf)CH$_2$Cl$_2$ and an allylpalladium chloride dimer; and the second catalyst is selected from one or more in a group formed by triphenylphosphine, tricyclohexylphosphonium tetrafluoroborate, tri-tert-butylphosphine, 1,1'-bis(diphenylphosphino)ferrocene, 1,2-bis(diphenylphosphinoyl)ethane, 1,3-bis(diphenylphosphinoyl)propane and 1,3-bis(diisopropylphosphino)propane.

Furthermore, the organic solvent is selected from one or more in a group formed by N,N-dimethylformamide, N,N-dimethylacetamide, N-methyl pyrrolidinone, N-ethyl pyrrolidinone, dimethyl sulfoxide and dioxane.

Furthermore, in the aminocarbonylation reaction process, a nucleophilic promoter is added into a reaction system of that, and the nucleophilic promoter is selected from one or more in a group formed by phenol, p-chlorophenol, naphthol and 4-methyl-1-naphthol.

Furthermore, an amount of the nucleophilic promoter is 0.17~300% of the mole number of the compound A.

Furthermore, in the aminocarbonylation reaction process, an acid-binding agent is added into the reaction system of that, and the acid-binding agent is selected from one or more in a group formed by triethylamine, N,N-diisopropylethylamine, N,N-dimethylaniline, DABCO (1,4-Diazabicyclo[2,2]octane), DBU (1,8-Diazabicyclo[5.4.0]undec-7-ene), pyridine, potassium carbonate, potassium phosphate, sodium carbonate and sodium phosphate; preferably a molar number of the acid-binding agent is 1~10 times to that of the compound A.

Furthermore, the C$_1$~C$_{10}$ alkyl is selected from methyl, ethyl, n-propyl, isopropyl, n-butyl, isobutyl, tert-butyl or cyclohexyl.

Furthermore, the C$_1$~C$_3$ alkoxy ethyl is selected from methoxyethyl, propoxyethyl or chloroethoxyethyl.

Furthermore, the C$_7$~C$_{19}$ aralkyl is selected from benzyl, p-nitrobenzyl, p-methoxybenzyl, benzhydryl or triphenylmethyl.

According to the technical solution of the disclosure, as a raw material, the compound A with the structure shown in formula I is reacted with the 3-(4-methyl-1H-imidazole-1-yl)-5-(trifluoromethyl) aniline to obtain the amination product. Then, the R group contained on the amination product is removed to obtain a target product nilotinib by virtue of the deprotection treatment. In the disclosure, the aminocarbonylation reaction is creatively applied to a route for synthesizing the nilotinib, and the preparation method is short in synthesis route and high in efficiency. More particularly, a nitrogen atom of an amino group of the compound A, adopted in the preparation method, contains a protective group R. This is favorable for avoiding a complexation reaction of the nitrogen atom on the amino group and another atom in the reaction system, thereby favorably promoting the aminocarbonylation reaction, improving a yield, simultaneously reducing preparation cost and improving economy.

BRIEF DESCRIPTION OF THE DRAWINGS

The drawings forming a part of the disclosure are adopted to provide a further understanding to the disclosure. Schematic embodiments of the disclosure and descriptions thereof are adopted to explain the disclosure and not intended to form improper limits to the disclosure. In the drawings:

FIG. 1 is a Nuclear Magnetic Resonance (NMR) spectrogram of nilotinib prepared according to embodiment 1 of the disclosure.

DETAILED DESCRIPTION OF THE EMBODIMENTS

It is important to note that the embodiments in the disclosure and characteristics in the embodiments may be combined under the condition of no conflicts. The disclosure will be described below in detail with reference to the embodiments.

As mentioned in the background, the problems of long route and relatively high cost of nilotinib synthesis in an existing process are required to be solved. For solving the problems, the disclosure provides a method for preparing nilotinib. The preparation method comprises the following steps: performing an aminocarbonylation reaction on a compound A and 3-(4-methyl-1H-imidazole-1-yl)-5-(trifluoromethyl)aniline to obtain an amination product; and performing R group deprotection treatment on the amination product to the nilotinib, wherein the compound A has a structure shown in formula I:

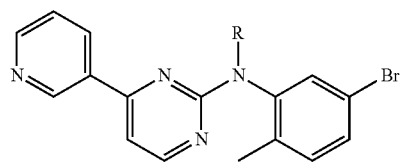

Formula I the R group includes, but not limited to, benzyl, —COCF$_3$, —CHO or —CO$_2$R', wherein an R' group includes, but not limited to, C$_1$~C$_{10}$ alkyl, C$_1$~C$_3$ alkoxy ethyl or C$_7$~C$_{19}$ aralkyl.

In the disclosure, the aminocarbonylation reaction is creatively applied to a route for synthesizing the nilotinib. Particularly, as a raw material, the compound A with the structure shown in formula I is reacted with the 3-(4-methyl-1H-imidazole-1-yl)-5-(trifluoromethyl) aniline to obtain the amination product. Then, the R group contained on the amination product is removed to obtain a target product nilotinib by virtue of the deprotection treatment. The preparation method is short in synthesis route and high in efficiency. More particularly, a nitrogen atom of an amino group of the compound A, adopted in the preparation method, contains a protective group R. This is favorable for avoiding a complexion reaction of the nitrogen atom on the amino group and another atom in a reaction system, thereby favorably promoting the aminocarbonylation reaction, improving a yield, simultaneously reducing preparation cost and improving economy.

In the preparation method, those skilled in the art may select a specific operating process for the carbonylation esterification reaction. In a preferred implementation mode, the carbonylation esterification reaction is performed on the compound A under a condition of existence of an organic solvent, a catalyst and a carbon monoxide, wherein a molar ratio of the 3-(4-methyl-1H-imidazole-1-yl)-5-(trifluoromethyl) aniline to the compound A is 0.5:1~2:1, and a using amount of the catalyst is 0.1~20% of a mole number of the compound A.

In the preparation method, the catalyst may be common species of the field. In a preferred implementation mode, the catalyst includes a first catalyst and a second catalyst, wherein the first catalyst includes, but not limited to, one or more in a group formed by PdCl$_2$(PPh$_3$)$_2$, PdCl$_2$(PhCN)$_2$, PdCl$_2$(CH$_3$CN)$_2$, Pd(PPh$_3$)$_4$, Pd$_2$(dba)$_3$CH$_2$Cl$_2$, PdCl$_2$(dppf)CH$_2$Cl$_2$ and an allylpalladium chloride dimer; and the second catalyst includes, but not limited to, one or more in a group formed by triphenylphosphine, tricyclohexylphosphonium tetrafluoroborate, tri-tert-butylphosphine, 1,1'-bis(diphenylphosphino)ferrocene, 1,2-bis(diphenylphosphinoyl)ethane, 1,3-bis(diphenylphosphinoyl)propane and 1,3-bis(diisopropylphosphino)propane. Compared with independent use of a palladium chloride catalyst, simultaneous use of the first catalyst and the second catalyst is favorable for enhancing an electron density of a palladium atom. As a result, a catalytic activity of the palladium chloride catalyst is further enhanced. In addition, the catalyst is low in cost and readily available, and adopting the catalyst is favorable for further reducing process cost. Preferably, a molar ratio of the first catalyst to the second catalyst is 1:0.5~1:4. Adopting the ratio is favorable for further improving the catalytic activity of the catalyst.

In the preparation method, the organic solvent may be a common species of the field. In a preferred implementation mode, the organic solvent includes, but not limited to, one or more in a group formed by N,N-dimethylformamide, N,N-dimethylacetamide, N-methyl pyrrolidinone, N-ethyl pyrrolidinone, dimethyl sulfoxide and dioxane. The organic solvent above has high solubility for all the reactants used in the disclosure, and may provide a stable reaction environment for the reactants.

In the preparation method, adopting the abovementioned process condition and raw material may shorten the reaction route, improve the yield of the nilotinib and simultaneously reduce the production cost. In a preferred implementation mode, in the carbonylation esterification reaction process, a nucleophilic promoter is added into the reaction system of that, and the nucleophilic promoter includes, but not limited to, one or more in a group formed by phenol, p-chlorophenol, naphthol and 4-methyl-1-naphthol. Compared with alkyl amines, an aromatic amine has relatively poor nucleophilicity. In the preparation method of the disclosure, the nucleophilic promoter is added in the carbonylation reaction process, so that the nucleophilicity of the aromatic amine may be improved, the reaction condition for the carbonylation esterification reaction is further reduced, and the reaction is milder and safer in operation. In addition, adopting the above nucleophilic promoters is favorable for further improving the nucleophilicity of the aromatic amine.

In the preparation method, those skilled in the art may select an amount of the nucleophilic promoter. In a preferred implementation mode, the amount of the nucleophilic promoter is 0.17~300% of the mole number of the compound A. Controlling the amount of the nucleophilic promoter within the range above is favorable for further improving the nucleophilicity of the aromatic amine and making the reaction condition milder.

In the preparation method, adopting the abovementioned process condition and raw material may shorten the reaction route, improve the yield of the nilotinib and simultaneously reduce the production cost. In a preferred implementation mode, in the aminocarbonylation reaction process, an acid-binding agent is added into the reaction system of that, and the acid-binding agent includes, but not limited to, one or more in a group formed by triethylamine, N,N-diisopropylethylamine, N,N-dimethylaniline, DABCO (1,4-Diazabicyclo[2.2.2]octane), DBU (1,8-Diazabicyclo[5.4.0]undec-7-ene), pyridine, potassium carbonate, potassium phosphate, sodium carbonate and sodium phosphate. An acidic byproduct may be formed in the carbonylation process. Adding the acid-binding agent may remove the acidic byproduct, thereby increasing the reaction rate. In addition, all reactions involved in the disclosure are organic reactions. During a practical operation, a desiccant is preferably added into the reaction system, and the water remover includes, but not limited to, one or more in a group formed by a 4 A molecular sieve, sodium sulfate, magnesium sulfate and a calcium oxide.

In the preparation method, those skilled in the art may select an amount of the acid-binding agent. In a preferred implementation mode, the acid-binding agent is 1~10 times the mole number of the compound A. Controlling the amount of the acid-binding agent within the range is favorable for further increasing the reaction rate of the carbonylation esterification reaction.

In a practical operating process, raw materials are preferably added into a reaction kettle at one time, then performing the carbonylation esterification reaction and amination reaction with a "one-pot method". Preferably, in a process of preparing the nilotinib in the disclosure, all the reactants, the solvent and the catalyst are added together into the reaction kettle, then CO is introduced into the reaction kettle, pressure is controlled to be 0.2~0.4 MPa, and a reaction temperature is controlled to be 80~110° C.

In the preparation method, those skilled in the art may select a type of the protective group R in the compound A as long as it may protect the nitrogen atom and may be removed by a later deprotection treatment. In a preferred implementation mode, the $C_1$~$C_{10}$ alkyl includes, but not limited to, methyl, ethyl, n-propyl, isopropyl, n-butyl, isobutyl, tert-butyl or cyclohexyl, the $C_1$~$C_3$ alkoxy ethyl includes, but not limited to, methoxyethyl, propoxyethyl or chloroethoxyethyl, and the $C_7$~$C_{19}$ aralkyl includes, but not limited to, benzyl, p-nitrobenzyl, p-methoxybenzyl, benzhydryl or triphenylmethyl. The abovementioned substituents are stable in chemical property, have good electron donating effects, and may be easily removed in a deprotection treatment process. Therefore, adopting the abovementioned substituents is favorable for improving stability of the compound A, and simultaneously makes the deprotection treatment process easy and convenient to operate.

In the preparation method, when different protective agents are introduced into the compound A, those skilled in the art may select a specific operation for the deprotection treatment. In a preferred implementation mode, when the R group is the benzyl, hydrogen is introduced into the system containing the amination product, which can remove the benzyl by hydrogenation. Then, a reaction solution is taken out, and the water remover is filtered to obtain a filtrate. Next, aqueous alkali at a mass concentration of 1% is added into the filtrate, and solids are precipitated by stirring. Finally, drying treatment is performed on the solids to obtain the nilotinib.

In another preferred implementation mode, when the R group is the —$COCF_3$ or the —CHO, the system containing the amination product is diluted with a Methyl Tert-Butyl Ether (MTBE) at first, and the water remover is filtered to obtain a filtrate. Then, aqueous alkali at a mass concentration of 10% is added into the filtrate, and solids are precipitated by stirring. Finally, the drying treatment is performed on the solids to obtain the nilotinib.

In another implementation mode, when the R group is a t-butyloxycarbonyl (Boc protective agent), the system containing the amination product is diluted with MTBE at first, and the water remover is filtered to obtain filtrate. Then, aqueous alkali at a mass concentration of 1% is added into the filtrate, and solids are precipitated by stirring. Next, the obtained solids are added into a trifluoroacetic acid, and the Boc protective agent is removed. Later on, the superfluous trifluoroacetic acid is removed by concentration, then ethanol is added, and crystallization is performed after heating and dissolving, and nilotinib trifluoroacetate is obtained. Then, the nilotinib trifluoroacetate is dissolved with the ethanol, a solution of KOH is added to regulate pH=6~9, and then the nilotinib may be dissociated. Finally, the system is filtered, washed and dried to obtain the nilotinib. Preferably, the aqueous alkali is an aqueous solution of $K_2CO_3$ or an aqueous solution of KOH.

When the R group is the —$CO_2R'$ and the R' group is the $C_1$~$C_{10}$ alkyl, the R group is removed by the following specific treatment steps: filtering solids from the aminocarbonylation reaction system, adding a 10% aqueous solution of the KOH, performing heating to 90~100° C., and after complete reaction (8 h), adding an excessive amount of water to precipitate a crude nilotinib product.

When the R group is the —$CO_2R'$ and the R' group is the $C_1$~$C_3$ alkoxy ethyl, the R group is removed by the following specific treatment steps: filtering solids from the aminocarbonylation reaction system, adding a 20% hydrochloric acid for a stirring reaction, and after tracking to complete reaction (3 h), adding a 20% aqueous solution of the KOH to precipitate a crude nilotinib product.

When the R group is the —$CO_2R'$ and the R' group is the $C_7$~$C_{19}$ aralkyl, the R group is removed by the following specific treatment steps: filtering solids from the aminocarbonylation reaction system, adding a solution of the KOH at a mass concentration of 10%, and performing stirring for 6 h at 40~50° C. to remove the protective group R. In the reaction solution, purified water (100 mL) is added to precipitate the solids.

The disclosure will be further described below in detail with reference to specific embodiments, and these embodiments may not be understood to limit the required scope of protection of the disclosure.

Embodiment 1

Dimethylformamide (1 L), 3-(4-methyl-1H-imidazole-1-yl)-5-(trifluoromethyl)aniline (aromatic amine, 0.54 mol), (5-bromo-2-methylphenyl(4-(pyridine-3-yl)pyrimidine-2-yl)-tert-butyl carbamate (0.648 mol), a 1,1'-bis(diphenylphosphino)ferrocene-palladium(II) dichloride dichloromethane complex (0.016 mol), triphenylphosphine (0.032 mol), phenol (2.5 g, 0.027 mol), triethylamine (1.62 mol) and a 4 A molecular sieve (100 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 42 h reaction, a product system containing an amination product is obtained. The product system is cooled to be below 50° C., and the carbon monoxide is evacuated and displaced with the nitrogen.

The product system is diluted with an MTBE (1 L), and the molecular sieve is filtered to obtain a filtrate. An aqueous solution of $K_2CO_3$ (10 L) at a mass concentration of 1% is added into the filtrate, and solids are precipitated by stirring. The solids are added into a trifluoroacetic acid (500 mL) to remove a Boc protective group. After the superfluous trifluoroacetic acid is removed by concentration, ethanol (2 L) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (249 g) is obtained by filtering, washing and drying, a yield being 87% and an NMR spectrogram of the product being shown in FIG. 1. A High Performance Liquid Chromatography (HPLC) purity of the product is measured to be 99%.

Embodiment 2

Dimethylformamide (10 mL), 3-(4-methyl-1H-imidazole-1-yl)-5-(trifluoromethyl) aniline (aromatic amine, 4.5 mmol), (5-bromo-2-methylphenyl(4-(pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 72 h reaction, a product system containing an amination product is obtained. The product system is cooled to be below 50° C., and the carbon monoxide is evacuated and displaced with the nitrogen.

The system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. A 4 mol/L hydrochloric acid (2 mL) is added to remove a Boc protective group by 4 h stirring. Ethanol (20 mL) is added into the reaction solution for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.7 g) is obtained by filtering, washing and drying, a yield being 72%. An HPLC purity of the product is measured to be 98%.

Embodiment 3

Dioxane (10 mL), 3-(4-methyl-1H-imidazole-1-yl)-5-(trifluoromethyl)aniline (aromatic amine, 4.5 mmol), (N-benzyl-N-5-bromo-2-methylphenyl(4-pyridine-3-yl)pyrimidine-2-amine (5.4 mmol), trans-dichlorobis(triphenylphosphine)palladium (0.135 mmol), 1,1'-bis(diphenylphosphino)ferrocene (0.135 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 65 h reaction, a product system containing an amination product is obtained. The product system is cooled to be below 50° C., and the carbon monoxide is evacuated and displaced with the nitrogen.

Hydrogen is introduced into the system to 2 MPa for hydrogenation benzyl removal. After 24 h reaction, the nitrogen is introduced to displace the hydrogen, and after the reaction solution is taken out, the molecular sieve is filtered. An aqueous solution of K2CO3 (100 mL) at a mass concentration of 1% is added into a filtrate, and solids are precipitated by stirring. Then, the solids are dried to obtain a nilotinib product (1.48 g), a yield being 62%. An HPLC purity of the product is measured to be 98%.

Embodiment 4

N-methyl pyrrolidinone (10 mL), 3-(4-methyl-1H-imidazole-1-yl)-5-(trifluoromethyl) aniline (aromatic amine, 4.5 mmol), (5-bromo-2-methylphenyl(4-(pyridine-3-yl) pyrimidine-2-yl)-tert-butyl carbamate (5.4 mmol), trans-dichlorobis(triphenyl-phosphine)palladium (0.135 mmol), a phosphorus ligand XantPhos (0.135 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 65 h reaction, a product system containing an amination product is obtained. The product system is cooled to room temperature, and the carbon monoxide is evacuated and displaced with the nitrogen.

The system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. A trifluoroacetic acid (4 mL) is added to remove a Boc protective group by 0.5 h stirring. Ethanol (20 mL) is added into the reaction solution for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.9 g) is obtained by filtering, washing and drying, a yield being 80%. An HPLC purity of the product is measured to be 99%.

Embodiment 5

Dimethylformamide (10 mL), 3-(4-methyl-1H-imidazole-1-yl)-5-(trifluoromethyl) aniline (aromatic amine, 4.5 mmol), N-(5-bromo-2-methylphenyl)-2,2,2-trifluoro-N-(4-(pyridine-3-yl)pyrimidine-2-yl)acetamide (5.4 mmol), a 1,1'-bis(diphenylphosphino)ferrocene-palladium (II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen to the pressure in the autoclave is increased to 0.8 MPa. A temperature is increased by heating to 90~105° C. for reaction. After 72 h reaction, a product system containing an amination product is obtained. The product system is cooled to be below 50° C., and the carbon monoxide is evacuated and displaced with the nitrogen.

The molecular sieve is filtered from the system with the amination product to obtain a filtrate. A solution of KOH (3 mL) at a mass concentration of 10% is added into the filtrate, and stirring is performed for 2 h at 40~50° C. to remove a trifluoroacetyl protective group. Purified water (100 mL) is added into the reaction solution to precipitate solids. The solids are dried to obtain a nilotinib product (2.0 g), a yield being 84%. An HPLC purity of the product is measured to be 98%.

Embodiment 6

Dimethylformamide (10 mL), 3-(4-methyl-1H-imidazole-1-yl)-5-(trifluoromethyl) aniline (aromatic amine, 4.5 mmol), (5-bromo-2-methylphenyl(4-(pyridine-3-yl) pyrimidine-2-yl)-methoxyethyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. A 4 mol/L hydrochloric acid (2 mL) is added to remove a protective group by 4 h stirring. Ethanol (20 mL) is added into the reaction solution for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.8 g) is obtained by filtering, washing and drying, a yield being 75%. An HPLC purity of the product is measured to be 98%.

Embodiment 7

Dimethylformamide (10 mL), 3-(4-methyl-1H-imidazole-1-yl)-5-(trifluoromethyl) aniline (aromatic amine, 4.5 mmol), (5-bromo-2-methylphenyl(4-(pyridine-3-yl) pyrimidine-2-yl)-ethyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The molecular sieve is filtered from the system with the amination product to obtain a filtrate. A solution of KOH (3 mL) at a mass concentration of 10% is added into the filtrate, and stirring is performed for 2 h at 40~50° C. to remove a protective group. Purified water (100 mL) is added into the reaction solution to precipitate solids. The solids are dried to obtain a nilotinib product (1.9 g), a yield being 80%. An HPLC purity of the product is measured to be 98%.

Embodiment 8

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-benzyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The molecular sieve is filtered from the system with the amination product to obtain a filtrate. A solution of KOH (3 mL) at a mass concentration of 10% is added into the filtrate, and stirring is performed for 6 h at 40~50° C. to remove a protective group. Purified water (100 mL) is added into the reaction solution to precipitate solids. The solids are dried to obtain a nilotinib product (1.8 g), a yield being 77%. An HPLC purity of the product is measured to be 98%.

Embodiment 9

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.045 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 96 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.7 g) is obtained by filtering, washing and drying, a yield being 70%. An HPLC purity of the product is measured to be 99%.

Embodiment 10

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbonate (5.4 mmol), a 1,1'-bis(diphenylphosphino) ferrocene-palladium(II) dichloride dichloromethane complex (0.135 mmol), triphenylphosphine (0.27 mmol), phenol (13.5 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 36 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.0 g) is obtained by filtering, washing and drying, a yield being 85%. An HPLC purity of the product is measured to be 99%.

Embodiment 11

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.2 MPa. A temperature is increased by heating to 90~105° C. for reaction, and the carbon monoxide is required to be timely supplemented. After 96 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.5 g) is obtained by filtering, washing and drying, a yield being 63%. An HPLC purity of the product is measured to be 98%.

Embodiment 12

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 4.0 MPa. A temperature is increased by heating to 90~105° C. for reaction. After 36 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.1 g) is obtained by filtering, washing and drying, a yield being 87%. An HPLC purity of the product is measured to be 99%.

Embodiment 13

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.0045 mmol), triphenylphosphine (0.009 mmol), phenol (0.0075 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 96 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.19 g) is obtained by filtering, washing and drying, a yield being 50%. An HPLC purity of the product is measured to be 98%.

Embodiment 14

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.9 mmol), triphenylphosphine (1.8 mmol), phenol (1.5 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 10 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.1 g) is obtained by filtering, washing and drying, a yield being 88%. An HPLC purity of the product is measured to be 99%.

Embodiment 15

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (4.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.6 g) is obtained by filtering, washing and drying, a yield being 68%. An HPLC purity of the product is measured to be 99%.

Embodiment 16

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (45 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.1 g) is obtained by filtering, washing and drying, a yield being 88%. An HPLC purity of the product is measured to be 99%.

Embodiment 17

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a bis(benzonitrile)palladium(II) chloride (0.135 mmol), 1,2-Bis(diphenylphosphine)ethane (DPPE) (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.38 g) is obtained by filtering, washing and drying, a yield being 100%. An HPLC purity of the product is measured to be 99%.

The system is diluted with the MTBE (10 mL), and the molecular sieve is filtered to obtain the filtrate. At first, an aqueous solution of $K_2CO_3$ (100 mL) at a mass concentration of 2% is added into the filtrate, and solids are precipitated by stirring. Then, acetonitrile (10 mL) is added into the solids, and beating purification is performed once to twice to obtain off-white solids. Next, a trifluoroacetic acid (5 mL) is added to remove a Boc protective group, the superfluous trifluoroacetic acid is removed by concentration, and ethanol (20 mL) is added for heating dissolving. Finally, crystallization is performed to obtain nilotinib trifluoroacetate. The nilotinib trifluoroacetate is dissolved with the ethanol, an aqueous solution of KOH is added to regulate pH=6˜9, and a nilotinib product (1.42 g) is obtained by filtering, washing and drying, a yield being 60%. An HPLC purity of the product is measured to be 99%.

Embodiment 18

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), allylpalladium chloride dimer (0.135 mmol), tricyclohexylphosphonium tetrafluoroborate (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.7 g) is obtained by filtering, washing and drying, a yield being 72%. An HPLC purity of the product is measured to be 99%.

Embodiment 19

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (9.0 mmol), 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.0 g) is obtained by filtering, washing and drying, a yield being 85%. An HPLC purity of the product is measured to be 99%.

Embodiment 20

Dimethylformamide (10 mL), 3-(4-methyl-1H-imidazole-1-yl)-5-(trifluoromethyl) aniline (aromatic amine, 9.0 mmol), (5-bromo-2-methylphenyl(4-pyridine-3-yl) pyrimidine-2-yl)-tert-butyl carbamate (4.5 mmol), 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.42 g) is obtained by filtering, washing and drying, a yield being 60%. An HPLC purity of the product is measured to be 95%.

Embodiment 21

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), 1,1'-bis(diphenylphosphino) ferrocene-palladium(II) dichloride dichloromethane complex (0.135 mmol), triphenylphosphine (0.27 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 96 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.2 g) is obtained by filtering, washing and drying, a yield being 50%. An HPLC purity of the product is measured to be 98%.

Embodiment 22

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.1 g) is obtained by filtering, washing and drying, a yield being 46%. An HPLC purity of the product is measured to be 99%.

Embodiment 23

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 120~140° C. for reaction. After 24 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (2.0 g) is obtained by filtering, washing and drying, a yield being 85%. An HPLC purity of the product is measured to be 99%.

Embodiment 24

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 80~90° C. for reaction. After 96 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.7 g) is obtained by filtering, washing and drying, a yield being 71%. An HPLC purity of the product is measured to be 99%.

Embodiment 25

Dimethylformamide (10 mL), 3-(4-methyl-1H-imidazole-1-yl)-5-(trifluoromethyl) aniline (aromatic amine, 4.5 mmol), (5-bromo-2-methylphenyl(4-pyridine-3-yl) pyrimidine-2-yl)-tert-butyl carbamate (5.4 mmol), a 1,1'-bis(diphenylphosphino) ferrocene-palladium(II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen and the pressure in the autoclave is increased to 0.8 MPa. A temperature is increased by heating to 90~105° C. for reaction. After 48 h reaction, a product system containing an amination product is obtained. The product system is cooled to be below 50° C., and the carbon monoxide is evacuated and displaced with the nitrogen.

The product system is diluted with an MTBE (10 mL), and the molecular sieve is filtered to obtain a filtrate. An aqueous solution of $K_2CO_3$ (100 mL) at a mass concentration of 1% is added into the filtrate, and solids are precipitated by stirring. The solids are added into a trifluoroacetic acid (5 mL) to remove a Boc protective group. After the superfluous trifluoroacetic acid is removed by concentration, ethanol (20 mL) is added for heating dissolving. Then, crystallization is performed to obtain nilotinib trifluoroacetate. The nilotinib trifluoroacetate is dissolved with the ethanol, an aqueous solution of KOH is added to regulate pH=6~9, and a nilotinib product (1.9 g) is obtained by filtering, washing and drying, a yield being 80%. An HPLC purity of the product is measured to be 99%.

Contrasting Example 1

Dimethyl sulfoxide (10 mL), 3-(4-methyl-1H-imidazole-1-yl)-5-(trifluoromethyl) aniline (aromatic amine, 4.5 mmol), N-5-bromo-2-methylphenyl(4-(pyridine-3-yl) pyrimidine-2-amine (5.4 mmol), 1,1'-bis(diphenylphosphino)ferrocene-palladium (II) dichloride dichloromethane complex (0.135 mmol), triphenylphosphine (0.27 mmol), phenol (0.225 mmol), triethylamine (13.5 mmol) and a 4 A molecular sieve (1 g) are added into an autoclave for uniform stirring. Nitrogen is introduced to displace air, and then a carbon monoxide is introduced to displace the nitrogen to and the pressure in the autoclave is increased to 0.8 MPa. A temperature is increased by heating to 90~105° C. for reaction. After 72 h reaction, a product system containing an amination product is obtained. The product system is cooled to be below 50° C., and the carbon monoxide is evacuated and displaced with the nitrogen.

The reaction solution is taken out, the molecular sieve is filtered, dichloromethane (100 mL×2) is added into a filtrate for beating purification, filtering is performed, and a filter cake is washed sequentially with a 10% solution of $K_2CO_3$ (30 mL×3) and purified water (50 mL). Drying is performed to obtain a product (13.8 g), a yield being 58% and an HPLC purity of the product being 99%.

From the above, it can be seen that the embodiments of the disclosure have the following technical effects.

(1) The protective group R (such as Boc) is introduced onto the nitrogen atom of the amino group of the raw material compound A, which avoids the metal palladium catalyst from being deactivated by the nitrogen atom, thereby reducing the using amount of the palladium catalyst.

(2) The nucleophilic promoter (such as the phenol) is added to increase a catalytic amount into an equivalent, thus a classical palladium-catalyzed aminocarbonylation reaction mechanism is changed (the classical mechanism refers to a direct aminocarbonylation reaction catalysis cycle, and is regulated to be divided into two catalysis cycles of carbonylation esterification and ester-amine exchange). So that an amide product may be generated from the aromatic amine [3-(4-methyl-1H-imidazole-1-yl)-5-(trifluoromethyl)aniline] with poor nucleophilicity under the mild temperature of within 100° C.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

The invention claimed is:
1. A method for preparing nilotinib, comprising the following steps:
performing an aminocarbonylation reaction on a compound A and 3-(4-methyl-1H-imidazole-1-yl)-5-(trifluoromethyl)aniline to obtain an amination product; and performing deprotection treatment of an R group on the amination product to obtain the nilotinib, wherein the compound A has a structure shown in formula I:

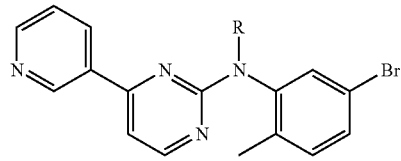

formula I in the formula I, the R group is selected from benzyl, —COCF₃, —CHO or —CO₂R', wherein an R' group is $C_1$~$C_{10}$ alkyl, $C_1$~$C_3$ alkoxy ethyl or $C_7$~$C_{19}$ aralkyl.

2. The preparation method of claim 1, wherein performing the aminocarbonylation reaction on the compound A under a condition which include an organic solvent, a catalyst and a carbon monoxide, wherein a molar ratio of the 3-(4-methyl-1H-imidazole-1-yl)-5-(trifluoromethyl)aniline to the compound A is 0.5:1~2:1, and the catalyst is 0.1~20% of a mole number of the compound A.

3. The preparation method of claim 2, wherein the catalyst comprises a first catalyst and a second catalyst, wherein
the first catalyst is selected from one or more in a group formed by $PdCl_2(PPh_3)_2$, $PdCl_2(PhCN)_2$, $PdCl_2(CH_3CN)_2$, $Pd(PPh_3)_4$, $Pd_2(dba)_3CH_2Cl_2$, $PdCl_2(dppf)CH_2Cl_2$ and an allylpalladium chloride dimer; and
the second catalyst is selected from one or more in a group formed by triphenylphosphine, tricyclohexylphosphonium tetrafluoroborate, tri-tert-butylphosphine, 1,1'-bis(diphenylphosphino)ferrocene, 1,2-bis(diphenylphosphinoyl)ethane, 1,3-bis(diphenylphosphinoyl)propane and 1,3-bis(diisopropylphosphino)propane.

4. The preparation method of claim 2 or 3, wherein the organic solvent is selected from one or more in a group formed by N,N-dimethylformamide, N,N-dimethylacetamide, N-methyl pyrrolidinone, N-ethyl pyrrolidinone, dimethyl sulfoxide and dioxane.

5. The preparation method of claim 1, wherein in the aminocarbonylation reaction process, adding a nucleophilic promoter into a reaction system of that, and the nucleophilic promoter is selected from one or more in a group formed by phenol, p-chlorophenol, naphthol and 4-methyl-1-naphthol.

6. The preparation method of claim 5, wherein an amount of the nucleophilic promoter is 0.17~300% of the mole number of the compound A.

7. The preparation method of claim 5, wherein in the aminocarbonylation reaction process, adding an acid-binding agent into the reaction system of that, and the acid-binding agent is selected from one or more in a group formed by triethylamine, N,N-diisopropylethylamine, N,N-dimethylaniline, DABCO, DBU, pyridine, potassium carbonate, potassium phosphate, sodium carbonate and sodium phosphate; preferably a molar number of the acid-binding agent is 1~10 times to that of the compound A.

8. The preparation method of claim 1, wherein the $C_1$~$C_{10}$ alkyl is selected from methyl, ethyl, n-propyl, isopropyl, n-butyl, isobutyl, tert-butyl or cyclohexyl.

9. The preparation method of claim 1, wherein the $C_1$~$C_3$ alkoxy ethyl is selected from methoxyethyl, propoxyethyl or chloroethoxyethyl.

10. The preparation method of claim 1, wherein the $C_7$~$C_{19}$ aralkyl is selected from benzyl, p-nitrobenzyl, p-methoxybenzyl, benzhydryl or triphenylmethyl.

11. The preparation method of claim 3, wherein the organic solvent is selected from one or more in a group formed by N,N-dimethylformamide, N,N-dimethylacetamide, N-methyl pyrrolidinone, N-ethyl pyrrolidinone, dimethyl sulfoxide and dioxane.

12. The preparation method of claim 2, wherein in the aminocarbonylation reaction process, a nucleophilic promoter is added into a reaction system of that, and the nucleophilic promoter is selected from one or more in a group formed by phenol, p-chlorophenol, naphthol and 4-methyl-1-naphthol.

13. The preparation method of claim 3, wherein in the aminocarbonylation reaction process, a nucleophilic promoter is added into a reaction system of that, and the nucleophilic promoter is selected from one or more in a group formed by phenol, p-chlorophenol, naphthol and 4-methyl-1-naphthol.

14. The preparation method of claim 4, wherein in the aminocarbonylation reaction process, a nucleophilic promoter is added into a reaction system of that, and the nucleophilic promoter is selected from one or more in a group formed by phenol, p-chlorophenol, naphthol and 4-methyl-1-naphthol.

15. The preparation method of claim 6, wherein in the aminocarbonylation reaction process, an acid-binding agent is added into the reaction system of that, and the acid-binding agent is selected from one or more in a group formed by triethylamine, N,N-diisopropylethylamine, N,N-dimethylaniline, DABCO, DBU, pyridine, potassium carbonate, potassium phosphate, sodium carbonate and sodium phosphate; preferably a molar number of the acid-binding agent is 1~10 times to that of the compound A.

16. The preparation method of claim 2, wherein the $C_1$~$C_{10}$ alkyl is selected from methyl, ethyl, n-propyl, isopropyl, n-butyl, isobutyl, tert-butyl or cyclohexyl.

17. The preparation method of claim 3, wherein the $C_1$~$C_{10}$ alkyl is selected from methyl, ethyl, n-propyl, isopropyl, n-butyl, isobutyl, tert-butyl or cyclohexyl.

18. The preparation method of claim 2, wherein the $C_1$~$C_3$ alkoxy ethyl is selected from methoxyethyl, propoxyethyl or chloroethoxyethyl.

19. The preparation method of claim 7, wherein the $C_1$~$C_3$ alkoxy ethyl is selected from methoxyethyl, propoxyethyl or chloroethoxyethyl.

20. The preparation method of claim 7, wherein the $C_7$~$C_{19}$ aralkyl is selected from benzyl, p-nitrobenzyl, p-methoxybenzyl, benzhydryl or triphenylmethyl.

* * * * *